United States Patent
Mucha

(10) Patent No.: US 10,398,512 B2
(45) Date of Patent: Sep. 3, 2019

(54) METHOD FOR GENERATING POSITION DATA OF AN INSTRUMENT

(76) Inventor: Dirk Mucha, Berlin (DE)

( * ) Notice: Subject to any disclaimer, the term of this patent is extended or adjusted under 35 U.S.C. 154(b) by 1154 days.

(21) Appl. No.: 13/321,087

(22) PCT Filed: May 17, 2010

(86) PCT No.: PCT/EP2010/002991
§ 371 (c)(1),
(2), (4) Date: Feb. 13, 2012

(87) PCT Pub. No.: WO2010/133320
PCT Pub. Date: Nov. 25, 2010

(65) Prior Publication Data
US 2012/0136626 A1 May 31, 2012

(30) Foreign Application Priority Data
May 18, 2009 (DE) .................. 10 2009 021 705

(51) Int. Cl.
*A61B 5/05* (2006.01)
*A61B 34/20* (2016.01)
(Continued)

(52) U.S. Cl.
CPC .............. *A61B 34/20* (2016.02); *A61B 5/062* (2013.01); *A61B 8/12* (2013.01);
(Continued)

(58) Field of Classification Search
CPC ......... A61B 5/06; A61B 8/12; A61B 19/5225; A61B 19/5244; A61B 19/44; A61B 19/54;
(Continued)

(56) References Cited

U.S. PATENT DOCUMENTS

| 5,840,024 A | * | 11/1998 | Taniguchi | ............ | A61B 1/0051 |
| | | | | | 600/424 |
| 2004/0024309 A1 | * | 2/2004 | Ferre | ...................... | A61B 34/20 |
| | | | | | 600/424 |

(Continued)

FOREIGN PATENT DOCUMENTS

| DE | 10 2004 017 834 A1 | 11/2005 |
| DE | 10 2006 052 886 A1 | 5/2007 |
| DE | 2004 017 834 A1 | 5/2007 |

OTHER PUBLICATIONS

Mucha, D. et al: Plausibility check for error compensation in electromagnetic navigation in endoscopic sinus surgery, Int. J. of Computer Assisted Radiology and Surgery (CARS), 2006, 316-318.

*Primary Examiner* — Jonathan Cwern
(74) *Attorney, Agent, or Firm* — Davidson, Davidson & Kappel, LLC

(57) ABSTRACT

A method for detecting deformations and errors and/or for generating position data of an instrument (1) with at least one first section (2) with at least one first sensor (4) and at least one second section (3) with at least one second sensor (5), wherein the method encompasses metrologically determining the position of the first and second sensor (4, 5). The method encompasses mathematically determining the position of the second sensor (5) with regard to the first section (2), preferably in at least two ways. Further, an apparatus for executing the method is specified.

5 Claims, 3 Drawing Sheets

(51) Int. Cl.
*A61B 5/06* (2006.01)
*A61B 8/12* (2006.01)
*A61M 25/01* (2006.01)
*A61B 90/00* (2016.01)

(52) U.S. Cl.
CPC ............... *A61B 2034/2051* (2016.02); *A61B 2034/2055* (2016.02); *A61B 2034/2068* (2016.02); *A61B 2090/061* (2016.02); *A61B 2090/0811* (2016.02); *A61M 25/0105* (2013.01)

(58) Field of Classification Search
CPC ............ A61B 19/50; A61B 2019/461; A61B 2019/5251; A61B 2019/5255; A61B 2019/5268; A61B 2019/4857; A61B 34/20; A61B 5/062; A61B 2034/2051; A61B 2090/0811; A61B 2090/061; A61B 2034/2068; A61B 2034/2055; G06F 15/00; G01R 33/285; A61M 25/0108; A61M 25/0105
See application file for complete search history.

(56) References Cited

U.S. PATENT DOCUMENTS

| | | | |
|---|---|---|---|
| 2005/0228270 A1* | 10/2005 | Lloyd | A61B 90/36 600/424 |
| 2005/0228274 A1 | 10/2005 | Boese et al. | 600/433 |
| 2006/0122497 A1 | 6/2006 | Glossop | 600/424 |
| 2007/0106114 A1* | 5/2007 | Sugimoto et al. | 600/117 |
| 2007/0135803 A1* | 6/2007 | Belson | 606/1 |
| 2007/0197896 A1* | 8/2007 | Moll et al. | 600/407 |
| 2008/0294034 A1* | 11/2008 | Krueger et al. | 600/409 |
| 2010/0121174 A1 | 5/2010 | Osadchy | 600/409 |

* cited by examiner

METHOD FOR GENERATING POSITION DATA OF AN INSTRUMENT

The present invention relates to a method for generating position data of an instrument and/or for detecting deformations of an instrument as well as an apparatus, a computer program product, a computer program according and a digital storage medium.

BACKGROUND

When working with an instrument in an area which cannot be clearly viewed, it may be of importance to record the current position of the instrument and present it in a suitable way. It is known to provide an instrument with electromagnetic position sensors, so-called coil elements. A field generator which is arranged in spatial proximity of the instrument generates an electromagnetic field which induces electric potential in the coil elements of the instrument according to the law of electromagnetic induction (induction law). The level of the induced potential or the electric currents (Ohm's law) in the coil elements may be different according to spatial position and positioning of the sensors at the instrument.

A control unit which is connected with the field generator and the position sensors may subsequently calculate the position of the sensors and thus of the instrument from the different measurement data of the field generator and the position sensors and, for example, present them on a monitor.

Also methods for determining the position of instruments which are based on optical measuring principles of suitable sensors on the instrument are known.

Methods of this sort are applicable for instruments which are rigid and do not deform or warp during use of the instruments. If methods of this sort are applied with instruments which warp during use, the position data cannot be clearly differentiated from possible interfering signals.

From DE 2004 017 834 A1, a catheter device encompassing a catheter to be introduced into a hollow organ, in particular a vessel, with several bending elements which are arranged to be spread along the longitudinal axis of the catheter and which are separately controllable as well as several communicating bending sensors which are arranged to be spread around the longitudinal axis of the catheter is known.

From DE 10 2006 052 886 A1, a system for recording the form of a flexible insertion portion of an endoscope, the system encompassing a position detection system which detects the positions of both ends of a bending section of the insertion portion, a means for determining the bending state of the bending section and a form reproduction processor for reproducing the bending section according to the recorded positions and the bending state is known.

SUMMARY OF THE INVENTION

It is an object of the present invention to provide a method which enables determining the position of at least one point on instruments with position sensors which may deform or warp during use.

The present invention provides a method for generating position data and/or for detecting deformations of a medical instrument with at least one first section with at least one first sensor and at least one second section with at least one second sensor, whereby the method encompasses determining the position of the first and second sensor metrologically; with the steps filing data which reflect allowable positions of the second sensor with regard to the first section mathematically determining the position of the second sensor with regard to the first section, comparing the mathematically determined position of the second sensor with the data on file, determining the absolute difference between the mathematically determined position of the second sensor and the data on file, setting an upper limit value for the absolute difference, and wherein mathematical determination of the position of the second sensor with regard to the first section takes place in at least two ways, wherein with one of the two ways, the metrologically determined first and second sensors recorded during use are not used.

In this method, the instrument comprises at least two different sections, a first and a second section. The shape or form of the two sections may be identical or different and is designed differently according to the application. Each of the two or more sections comprises at least one sensor each.

The position of the second sensor which is on or in the second section of the instrument is mathematically determined in relation to the first section, or, to put it differently, is calculated by means of a mathematical equation or a system of equations.

A deformation or distortion is in some embodiments described here in the sense that the second section changes its position in relation to the first section. According to the geometry and material properties of the instrument, according to physical ambient parameters such as for example temperature and pressure as well as according to the expected acting forces and moments at the instrument, it may be possible to mathematically describe or sufficiently precisely approximate the expected deformation or distortion.

In certain embodiments according to the invention, the mathematical determination of the position of the second sensor in relation to the first section is carried out in at least two ways, wherein one way does not use the metrologically determined positions of the first and the second sensor which are recorded during use.

In some embodiments according to the invention, the first way concerns or is establishing the relation with mathematical methods from position data from the metrological detection of the first and the second sensor at the time of application.

In certain embodiments according to the invention, the second way concerns or is a mathematical description of the possible positions the second sensor may assume in relation to the first sensor, if the mechanical restrictions which are imposed by the connection between the first and the second section are considered. The complete or sufficient mathematical description is available at the time of use, e.g., it is filed in a storage device.

This description may be for example a formal mathematical description in the form of an equation of a trajectory or a spreadsheet with discrete positions. Positions between two entries of the spreadsheet are determined by means of the interpolation method.

The description of the position can take place by means of
metrological methods, and/or
derivation of the trajectory from the mechanical properties of the instrument, and/or
simulation with mathematical methods.

"With regard to the first section" means that the position of the second sensor is calculated relative to the first section, e.g., with regard to a certain spot or area—such as for example the end of the first section.

Knowing the positional relation between the first and the second section of the instrument or between the second sensor and the first section, the positional relation being determinable according to the invention, in addition to further advantages, testing received position data for plausibility and/or calculating the existing deformation or distortion of the instrument and/or determining the actual position of, e.g., the tip or the tool section of the instrument also when being deformed due to its use is advantageously possible.

The electromagnetic position sensors, all or at least one of them, may in some embodiments according to the invention be so-called saturation-core magnetometers which output a signal which is proportional to the locally occurring field strength of the generated electromagnetic field.

Each of the provided sensors may be arranged on the surface of the instrument or within the instrument or the sections. For example, it may be advantageous to encapsulate at least one sensor in the instrument if it is not supposed to come in contact with the surroundings. This may serve either to protect the sensor from the surrounding medium, but also vice versa to protect the surrounding medium or surrounding tissue from the sensor. Possible applications are measurements in toxic and/or aggressive substances which could destroy the sensor or applications in the surroundings of human or animal tissue which can be influenced by sensor materials.

The sensors, which may also be denoted as position sensors, may measure or work based on different physical measuring principles.

As preferred embodiment, electromagnetic sensors are used. This offers the advantage that, for example as compared to optical sensors, the sensors can be used within different media, housings or encapsulations without a direct visual contact being necessary. Dealing with toxic substances or with devices or machines which are difficult to access, encapsulation is often necessary.

On the other hand, the possible interference of the medium or the application surroundings by electromagnetic fields is to be considered. Thus, also other measuring principles can be used for the sensors, for example optical methods by means of laser light.

Further methods with electromagnetic wavelength ranges which are for example close to the spectrum that is visible for humans (light), such as, e.g., infrared or ultraviolet radiation, may also be used.

Furthermore, the sensors which are located on the first section may differ from the sensors of the second section. Hereby, the sensor on the first section may be denoted as main sensor, the sensor on the second section may be denoted as secondary sensor, or vice versa. The main sensor may differ from the secondary sensor in its dimensions, in its sensitivity, measuring accuracy, the housing materials of the sensor and other features. Also the—in particular physical—measuring principles of the main sensor and the secondary sensor may be different. The main sensor may, e.g., be based on an optical measuring principle, the secondary sensor, e.g., on an electromagnetic measuring principle.

It is also possible that a main sensor is arranged on the instrument on the first section, and several secondary sensors on the second section. In the case of several secondary sensors, for each one an individual bending pattern or an individual bending line (corresponds to the curve of all locations or positions of the respective secondary sensor which are possible in the pattern) can be determined and saved, if required. The bending patterns and the bending lines may differ.

The metrological determination of the position of the sensors depends on the utilized measuring principles of the sensors and will not be discussed in further detail here, as it is sufficiently well known to the person skilled in the art.

Variables of the mathematical equation(s) for the determination of a location or position of a spot or an area of the first section with regard to the location or position of the second sensor are preferably three variables which are specified hereafter. The first variable determines the location or position of a point or an area of the first section with regard to the location or position of the first sensor on the first section. The second variable determines the measured location or position of the first sensor with regard to the measurement system. The third variable determines the location or position of the second sensor with regard to the measurement system. Preferably, the variables are illustrated as homogenous transformation matrices and the first variable is multiplied with the second variable and the result is multiplied with the inverse of the third variable. The result of this equation determines the position of the second sensor on the second section with regard to the first section.

The mathematical equation may, e.g., be in a preferred embodiment as follows:

$$^{Tcp}T_N = {^{Tcp}T_H} * {^H T_{Mess}} * ({^N T_{Mess}})^{-1}\text{—for homogenous transformation matrices}$$

Here, the following applies:

N secondary sensor
H main sensor
TCP tip of the instrument
Mess measuring value
T homogenous transformation matrix
$^{Tcp}T_N$ spatial relation between the tip of the instrument (TCP) and the secondary sensor
$^{Tcp}T_H$ spatial relation between the tip of the instrument (TCP) and the main sensor
$^H T_{Mess}$ position measurement data of the main sensor
$^N T_{Mess}$ position measurement data of the secondary sensor In a preferred embodiment, the invention encompasses in an advantageous development the filing of data which reproduce the position of the second sensor with regard to the first section in possible applications.

These filed data may be denoted as, e.g., function $T_{soll}$ and describe the relations between the tip of the instrument and secondary sensors.

The present invention relates in particular to determining the position of instruments which warp during use, due to an intended or an unintended distortion or deformation of the instrument. A distortion is described here in the sense that the second section changes its position with regard to the first section. According to the geometry and material properties of the instrument, according to physical ambient parameters such as for example temperature and pressure as well as according to the expected acting forces and moments at the instrument, it may be possible to mathematically describe or sufficiently precisely approximate the expected distortion. This means that position data can be filed which describe for example the possible spatial coordinates or relative coordinates between the first and the second section or between the first and the second sensor or between one of the sections and one of the sensors during a desired or undesired deformation. By means of the filed data, it may be tested whether measured position changes or deformations match the filed data or are within their range. In case of deviations, the amount of the deviation can be determined in order to subsequently test different causes or reject certain results of the position determination.

These data may for example be or get filed on a computational unit or a computer. This computer may preferably be used for recording the measurement data of the sensors and subsequent determination of the position of the sensors at the same time.

Furthermore, it is possible to use several instruments and several filed sets of data in an application. Allocating the instruments and the sets of data then for example takes place by means of identification numbers of the instruments and the associated filed data. Allocating may for example be carried out by means of a computational unit and a database. The filed data may be filed in a memory in the computational unit or in an external memory. The method for generating the position data may then be applied to the different instruments and filed data.

The filed data may, however, also stem from a method which preceded the method according to the invention. For example, they may already be delivered by the producer of the utilized instrument when purchased and be available in filed form.

In an again preferred embodiment of the method according to the invention, the filed data (independent of whether they were collected and filed by means of the method according to the invention or in an unrelated way) which reproduce the allowable positions of the second sensor with regard to the first section during possible applications of the instrument serve to evaluate the data which were collected by means of the mathematical formula based on actual measurements.

Thus, for example three parameters which describe the measurement data of the first and the second sensor as well as the position of the second sensor with regard to the first section can be determined. In the ideal case, these data should be the same. This would mean that the filed data, i.e. the theoretically possible position data of the instrument, exactly match the position data which were determined based on measurement data.

In fact, however, these theoretically determined position data and the position data which were determined based on the actually available measurement data during application may deviate from each other. Thus, in one embodiment of the method according to the invention, it is proposed to first determine an absolute difference between these data. As this is a measure only for determination of the absolute deviation, however, not of the direction of the deviation (theoretical data in comparison to measurement data), preferably only the absolute difference is considered again. Accordingly distinctive deviations may provide a first hint on different cause variables, measurement errors, interference variables or other artifacts of the position determination by means of the measurement data.

Therefore, in a further preferred embodiment of the method according to the invention, it is further proposed to define an upper limit value of the absolute difference after each series of measurements or generating of position data of an instrument. Above this limit value, the position data collected based on the measurements may be interpreted as data which were influenced in all probability by measurement errors, interference variables or other facts. It is in this case advantageously possible to draw suitable conclusions from this knowledge.

In an again further preferred embodiment of the method according to the invention, an instrument is used in which a joint element or bending element between the two sections (or between two sections in general) is provided. A bending element may be, e.g., a ball joint. This offers the advantage that a mathematical description of the possible positions of the second section with regard to the first section may be depicted as, e.g., elliptical paraboloid based on the knowledge of the limited bending possibility—especially if the bending element is suitably chosen—in a clear and possibly particularly easy way. This mathematical description may again be filed on a computer and compared with determined measurement positions.

In an again further preferred embodiment of the method according to the invention, an instrument is used in which a spatial limitation of the second section is provided. This spatial limitation may for example be achieved in a constructional way as the instrument comprises a mechanical stop. Thus, the possible positions of the instrument are limited which may be advantageous during use, e.g., when conducted through narrow tubes or pipes. This spatial limitation is taken into account as boundary conditions in the mathematical description of the possible positions.

In an again further preferred embodiment, the utilized instrument comprises a fixed connection between the first and the second section. Thus, the possible positions of the second section are significantly restricted. The possible positions are then for example influenced by external forces and moments on the rigid instrument. These deformations which are often unintended during use are mostly reversible (elastic), but dependent on the material properties, the physical ambient parameters such as temperature and pressure and the occurring forces and moments.

In an again further preferred embodiment, the spatial allocations of the sensors and possible reference points both during the measurements and during the mathematical descriptions are illustrated as homogenous transformation matrices. Thus, all spatial relations both for the measurement positions and for the mathematical descriptions can be sufficiently illustrated or mathematically mapped.

In an again further preferred embodiment of the invention, the position data, which were measured by means of the sensors, and a possible subsequent processing in a control unit or in a computer are output on a suitable output device. An output device of this sort may be, for example a monitor.

Here, it may be useful to not output measurement data which significantly deviate from the possible position data which were previously theoretically determined and are outside a limit value which was previously defined. This may be realized, e.g., by means of a threshold value filter in a control unit. This offers the advantage that a falsification—in particular an obvious one—of the position data by values that are above a defined limit value is not output on a display unit and is thus not visible.

The present invention encompasses also providing more than only one threshold value.

A further possibility which is proposed according to the invention is to correct values which are outside a defined limit value with a suitable method and subsequently output them. Possible correction algorithms are known to the person skilled in the art and are not further described here. Nevertheless, those are in connection with the features and feature combinations as described herein explicitly to be understood as disclosed.

Both the non-output of measurement values above a limit value and the correction and subsequent output of the measurement values for position determination of the instrument may be suitable to advantageously increase the accuracy of the position determination of instruments and the reliability regarding the output of the actual position of the instrument. The influence—especially the one which is unnoticed—by objects in the surroundings of the instrument, more precisely in the measurement area of the sensors on the instrument, is advantageously decreased by means of the described method. With the described electromagnetic sensors (coil elements), this applies for example to the influence by objects which feature ferromagnetic properties. The field distortion by these objects or their influence on a position determination is decreased by the mentioned method, in particular for non-rigid instruments which are suitable for intended deformations, and for rigid, but deformable instruments with position sensors.

In an again further preferred embodiment, the method according to the invention is used with medical instruments. For example, in oral and maxillo-facial surgery and in the otorhinolaryngology, it may be very important during surgery to know the exact position of operation instruments in order to not harm vessels, nerves or other sensitive areas. At the same time, during surgeries of this kind, a multitude of instruments, monitoring and diagnosis devices and other aids are used for the surgery. Often, a multitude of these instruments and devices is made of metallic materials, for example in order to achieve visibility on computer tomographies. Another reason for the utilization of metallic materials in operation instruments, which is common today, is the good sterilizability which is of great importance especially in the medical sector. On the other hand, new operative surgical techniques such as for example minimally invasive surgery are found in ever-increasing fields of application which often require precise navigation and guidance of instruments in areas which cannot be clearly viewed. Also in the above-mentioned fields of application, the method according to the invention offers great advantages as compared to the methods known from the state of the art.

The utilized instrument may be for example an ultrasonic probe (rectal probe, vaginal probe, intravascular probe), a catheter, an aspirator or a pointing instrument. Often, it can be advantageous if at least one section comprises a geometrically defined end in order to be suitably applicable, e.g., as a pointing instrument. With an ultrasonic probe, it may be advantageous if the probe is arranged at the end of a section. According to the shape of the probe, the end may be designed to be rounded, angular or pointed. Instruments with more than two sections are also possible, if for example several functions, geometries or measurement tasks should be carried out.

With the aid of the method according to the invention, it is advantageously possible to describe the position determination of instruments which change shape or warp during use, and/or to inform of detected artifacts or to take them into account in a position determination.

Advantageously, in certain embodiments according to the invention, interferences with the position measurement, be that distortions of the instrument or interferences by interfering objects which influence the measurement process, can be detected and eliminated.

For instruments which distort during use, be that an intended or an unintended distortion or deformation of the instrument, there is as of yet no method known to detect interferences to the position measurement caused by interfering objects separately from the deformations or bending and to eliminate them. The need for this is advantageously satisfied by some embodiments according to the invention.

In particular, it is advantageously possible by means of the method according to the invention to point out the existence of invisible objects in the spatial measurement data range or area—especially for the user or operator—which influence the metrological determination of the position of the sensors. If the sensors are based on, for example, electromagnetic operating principles, an influence of this kind can be caused by objects which are made of ferromagnetic materials. But also other metallic materials can influence the measurement result. The amount of influence, i.e. a change in quantity of the measurement signals, depends on different factors such as for example the close proximity of the objects to the sensors. The metrological position determination of the sensors and thus of the whole instrument can thus change if objects of this kind are present. These phenomena may lead to artifacts when determining the position of the instrument or a section hereof (e.g., its tip). Interferences of this kind may, however, be advantageously detected and/or corrected by means of the method according to the invention.

Hereby, the apparatus may comprise a tip of the instrument as an end of the first section as reference point for generating the position data of the instrument. This offers the advantage that, for example during use as a pointing instrument, the tip of the instrument is particularly suitable as reference point.

Furthermore, the apparatus may comprise a first and a second section which are each constructed to be rigid. This offers the advantage that in case of a deformation one sensor each is sufficient on each section for the position determination of the instrument.

BRIEF DESCRIPTION OF THE DRAWINGS

Hereafter, the method according to the invention is exemplarily described with reference to the appended figures in which identical reference numerals refer to same or similar components. In the partly highly simplified figures it applies that.

DETAILED DESCRIPTION

Figure 1:
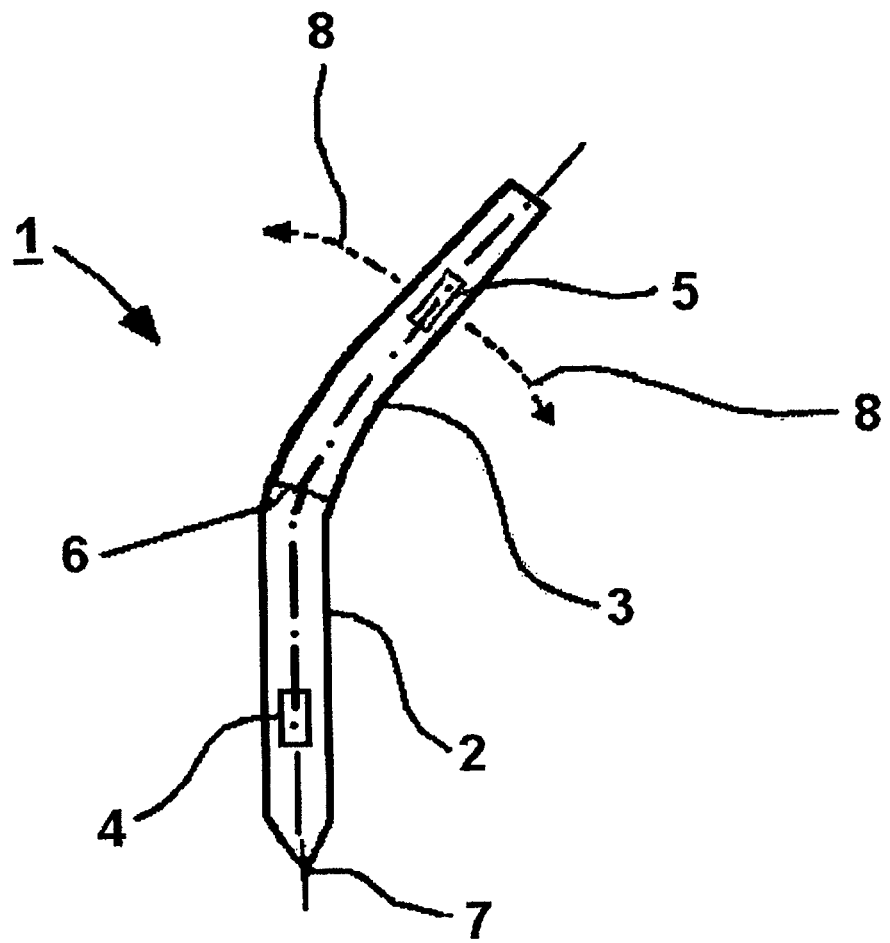
FIG. 1 shows a schematical overview of an exemplary arrangement for executing the method according to the invention.

FIG. 1 shows a cylindrical instrument 1 with a first section 2 and a second section 3. At the first section 2, a first sensor 4 is located, at the second section 3, a second sensor 5 is located. Both sensors 4, 5 are schematically shown on the surface of the instrument, however, they may be also located in an interior (not illustrated) of each the section 1, 2.

The first section 2 is firmly connected with the second section 3, for example by means of an adhesive seam or bond seam 6. However, it is also possible that the two sections 2 and 3 are made of one piece, in this case no joint or parting line would be visible. An end of the first section 2 is illustrated as conical or tapered tip of the instrument 7.

The instrument 1 is shown in FIG. 1 in a deformed condition. As opposed to the section 2, the section 3 is illustrated to be clearly bent. The bending point around which the section 3 is bent as opposed to section 2, is the bond seam 6. Both the section 2 and the section 3 are in contrast designed to be mostly rigid. The sensors 4 and 5 are located in the areas of the sections 2 and 3 which are not bent. The junction between this rigid and not deformed area of the sections 2 and 3 and the bent area in the area of the bond seam spot 6 is smooth and is not clearly defined.

Possible deformation conditions of the instrument 1 are illustrated by means of the possible spatial position of the sensor 5 and are denoted as bending line 8. Here, the possible positions of the sensor 5 can be described by means of suitable mathematical functions for which the tip of the instrument 7 is chosen as reference point here.

Figure 2:
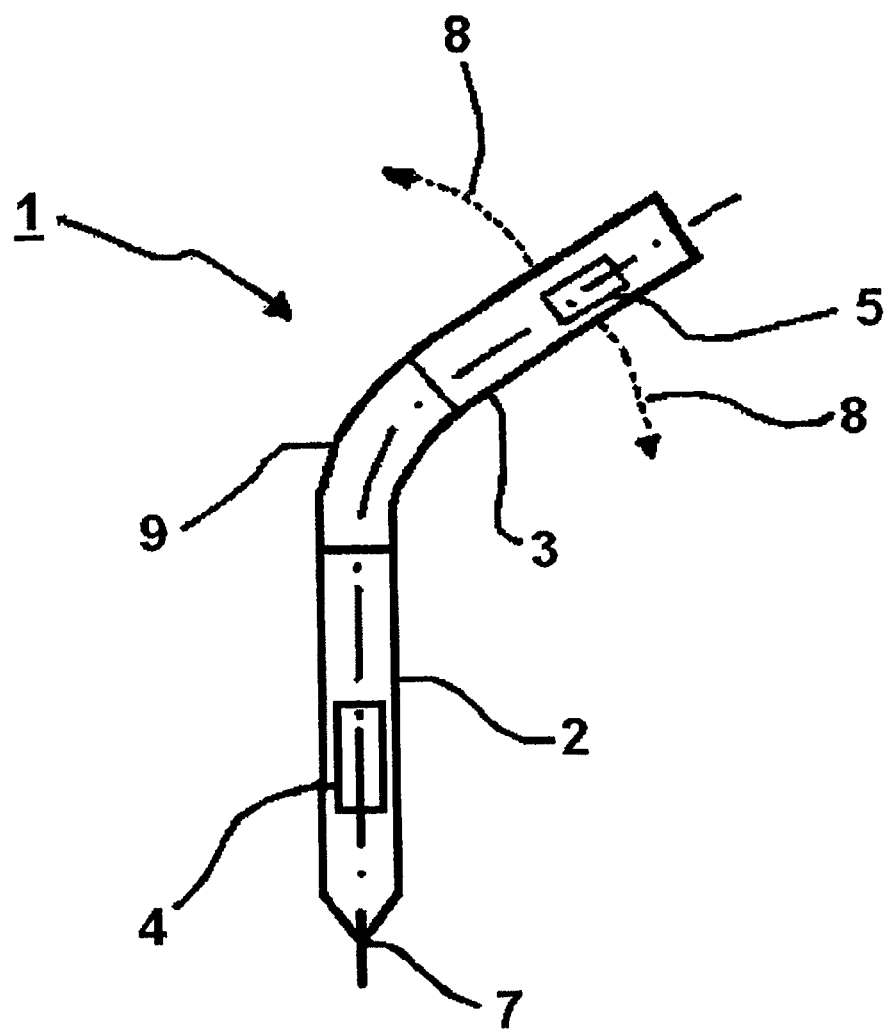
FIG. 2 shows a schematical overview of a further exemplary arrangement for executing the method according to the invention.

In FIG. 2, also a cylindrical instrument 1 with a first section 2 and a second section 3 is illustrated. The sensors 4 and 5 are located on the sections 2 and 3 in the same way as in FIG. 1. In contrast to FIG. 1, however, a bending element 9 is arranged between the sections 2 and 3. This bending element 9 has the function to be able to reproduce the deformation or the bending of the section 3 with respect to the tip of the instrument 7 as reference point of the section 2 in a predictable and mathematically describable function. This function is described as the mathematical formula of the bending line 8.

As bending elements 9, for example mechanical joints can be used. When using a ball joint, the bending line 8 can be mathematically described as elliptical paraboloid. Further possible are for example also elastic polymeric materials as bending elements 9 which would allow deformations or distortions in this area in a targeted manner.

Figure 3:
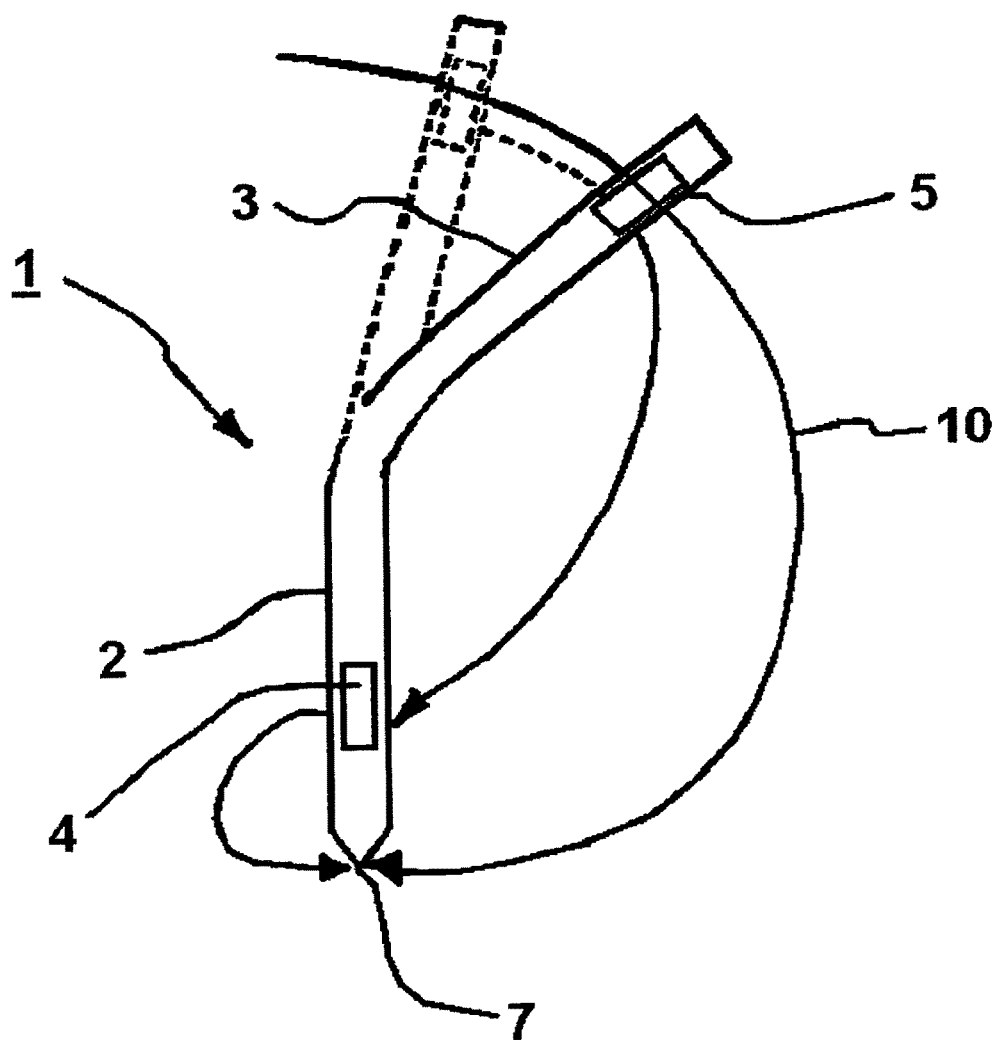
FIG. 3 shows a schematical overview of a further exemplary arrangement for executing the method according to the invention.

In FIG. 3, a path line 10 is illustrated, which shows the possible positions of the secondary sensor.

What is claimed is:

1. A method for generating and displaying position data and/or for detecting deformations of a medical instrument including a first section with a first sensor and a second section with a second sensor, the first sensor being an electromagnetic or an optical sensor and the second sensor being an electromagnetic or an optical sensor, the method including determining a position of the first and second sensor metrologically, the method comprising:
    filing data reflecting allowable positions of the second sensor during possible applications of the instrument, the allowable positions of the second sensor being calculated relative to the first section, the allowable positions being a mathematical description of positions the second sensor may assume relative to the first section due to a capability of deformation of the instrument;
    mathematically determining the position of the second sensor relative to the first section from the metrologically determined position of the first and second sensor;
    comparing the mathematically determined position of the second sensor with the data on file;
    determining an absolute difference between the mathematically determined position of the second sensor with regard to the first section and the data on file to define mathematically determined position data of the second sensor;
    setting an upper limit value for the absolute difference such that values above the upper limit value indicate positions the instrument is incapable of being deformed into during use;
    identifying the mathematically determined position data of the second sensor outside the upper limit value as data influenced by measurement error or interference; and
    displaying, by an output device, the mathematically determined position of the second sensor as a function of the identified data influenced by measurement error or interference, the displaying including one of:
        displaying the mathematically determined position of the second sensor by the excluding of the data influenced by measurement error or interference, or
        first correcting the data influenced by measurement error or interference, and then displaying the mathematically determined position of the second sensor with the corrected data.

2. The method as recited in claim 1 wherein a tip of the instrument is a reference point for generating position data of the first section of the instrument.

3. The method as recited in claim 1 wherein spatial allocation of at least one of the first and second sections and at least one of the first and second sensors are described as homogenous transformation matrices.

4. The method as recited in claim 1 further comprising pointing out the existence of invisible objects in the spatial measurement data range or area influencing the metrological determination of the position of the sensors.

5. A computer program product, disposed on a non-transitory computer readable media, for generating and displaying position data and/or for detecting deformations of a medical instrument including a first section with a first sensor and a second section with a second sensor by determining a position of the first and second sensor metrologically, the first sensor being an electromagnetic or an optical sensor and the second sensor being an electromagnetic or an optical sensor, the computer program product including a program code which is configured for executing the following steps when the computer program runs on a computer:
    filing data reflecting allowable positions of the second sensor during possible applications of the instrument, the allowable positions of the second sensor being calculated relative to the first section, the allowable positions being a mathematical description of positions the second sensor may assume relative to the first section due to a capability of deformation of the instrument;
    mathematically determining the position of the second sensor relative to the first section from the metrologically determined position of the first and second sensor;
    comparing the mathematically determined position of the second sensor with the data on file;
    determining an absolute difference between the mathematically determined position of the second sensor with regard to the first section and the data on file to define mathematically determined position data of the second sensor;
    setting an upper limit value for the absolute difference such that values above the upper limit value indicate positions the instrument is incapable of being deformed into during use;
    identifying the mathematically determined position data of the second sensor outside the upper limit value as data influenced by measurement error or interference; and
    displaying, by an output device, the mathematically determined position of the second sensor as a function of the identified data influenced by measurement error or interference, the displaying including one of:
        displaying the mathematically determined position of the second sensor by the excluding of the data influenced by measurement error or interference, or
        first correcting the data influenced by measurement error or interference, and then displaying the mathematically determined position of the second sensor with the corrected data.

* * * * *